(12) United States Patent
Thornburg

(10) Patent No.: US 9,381,008 B2
(45) Date of Patent: Jul. 5, 2016

(54) RETRACTOR DEVICE

(71) Applicant: Lauren Chase Thornburg, Atlanta, GA (US)

(72) Inventor: Lauren Chase Thornburg, Atlanta, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/199,221

(22) Filed: Mar. 6, 2014

(65) Prior Publication Data

US 2015/0250466 A1 Sep. 10, 2015

(51) Int. Cl.
*A61B 17/02* (2006.01)

(52) U.S. Cl.
CPC .................... *A61B 17/0206* (2013.01)

(58) Field of Classification Search
USPC .................................. 600/224, 208
See application file for complete search history.

(56) References Cited

U.S. PATENT DOCUMENTS

| 350,721 | A | * | 10/1886 | Cooper | 600/224 |
|---|---|---|---|---|---|
| 3,724,449 | A | * | 4/1973 | Gauthier | A61B 17/0293 600/215 |
| 5,681,265 | A | * | 10/1997 | Maeda et al. | 600/219 |
| 5,931,777 | A | * | 8/1999 | Sava | 600/213 |
| 6,074,343 | A | * | 6/2000 | Nathanson et al. | 600/214 |
| 6,196,969 | B1 | * | 3/2001 | Bester et al. | 600/224 |
| 6,342,036 | B1 | * | 1/2002 | Cooper | A61B 1/32 600/224 |
| 7,052,457 | B2 | * | 5/2006 | Fanous | A61B 17/0293 600/220 |
| 7,481,766 | B2 | * | 1/2009 | Lee et al. | 600/214 |
| 7,850,608 | B2 | | 12/2010 | Hamada | |
| 7,931,589 | B2 | | 4/2011 | Cohen | |
| 8,303,499 | B2 | | 11/2012 | Hamada | |
| 8,353,826 | B2 | | 1/2013 | Weiman | |
| 2005/0080320 | A1 | * | 4/2005 | Lee et al. | 600/214 |
| 2007/0100212 | A1 | | 5/2007 | Pimenta | |
| 2009/0018399 | A1 | | 1/2009 | Martinelli | |
| 2011/0224497 | A1 | | 9/2011 | Weiman | |
| 2013/0345520 | A1 | | 12/2013 | Hamada | |

* cited by examiner

*Primary Examiner* — Jan Christopher Merene
(74) *Attorney, Agent, or Firm* — David L. King

(57) ABSTRACT

A retractor device has a first arm rotatable arcuately about a first pivot; a second arm rotatable arcuately about a second pivot; and a third arm interposed between the first and second arm. The third arm has a linearly movable blade holding end translatable inwardly and outwardly between the first and second arms. The third arm is connected to the first arm at the first pivot and the second arm at the second pivot. The first arm and said second arm are rotatably movable about their respective pivot independent of the other arm.

5 Claims, 6 Drawing Sheets

RETRACTOR DEVICE

TECHNICAL FIELD

The present disclosure relates to methods and devices for retracting tissue in a surgical procedure to allow access to the surgical site.

BACKGROUND OF THE INVENTION

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray. One typical retractor system may include a plurality of blades coupled to a refractor frame. In use, the blades may be inserted into an incision and then retracted to displace tissue surrounding the incision exposing the surgical site. To minimize trauma to the tissue, this tissue displacement should be refined and controlled. However, current refractor systems do not provide desired control of the distraction. More particularly, the devices currently in use are mechanically coupled so the surgeon has limited ability to feel the resistance at the blades or to rotate the blades affixed to the retractor arm independently. This limited control takes away the skilled surgeon's ability to finely adjust the movement of the retractor blades.

Thus there is a need for improved methods and devices that can be used for retracting tissue to provide access to the surgical site.

SUMMARY OF THE INVENTION

A retractor device has a first arm rotatable arcuately about a first pivot; a second arm rotatable arcuately about a second pivot; and a third arm interposed between the first and second arm. The third arm has a linearly movable blade holding end translatable inwardly and outwardly between the first and second arms. The third arm is connected to the first arm at the first pivot and the second arm at the second pivot. The first arm and said second arm are rotatably movable about their respective pivot independent of the other arm.

In a preferred embodiment, the third arm has a handle end opposite the blade holding end. The handle end is connected to move the linearly movable blade holding end.

Each of the first and second arms each has a blade holding end and an opposite handle end wherein movement of each respective handle inwardly pivots the blade holding end arcuately about the respective pivot. Each first or second arm movement is independently movable relative to the other. Each first and second arm has a spring loaded adjustment screw fixed to the third arm to set or limit inward movement at the respective blade holding end. The spring of each of the adjustment screws bias the respective first and second arm about said pivot toward a more open position. Tightening an adjustment screw moves said blade end of the first or second arm about said pivot outwardly.

Independent movement of said first arm relative to said second arm or said second arm relative to said first arm is provided by holding said third arm handle and moving said first or second arm toward said third arm handle while said opposite arm is unmoved. Simultaneous movement of said first and second arm is achieved by grasping both handle ends of said first and second arm and squeezing together toward said third arm.

BRIEF DESCRIPTION OF THE DRAWINGS

The invention will be described by way of example and with reference to the accompanying drawings in which.

DETAILED DESCRIPTION OF THE INVENTION

Figure 1:
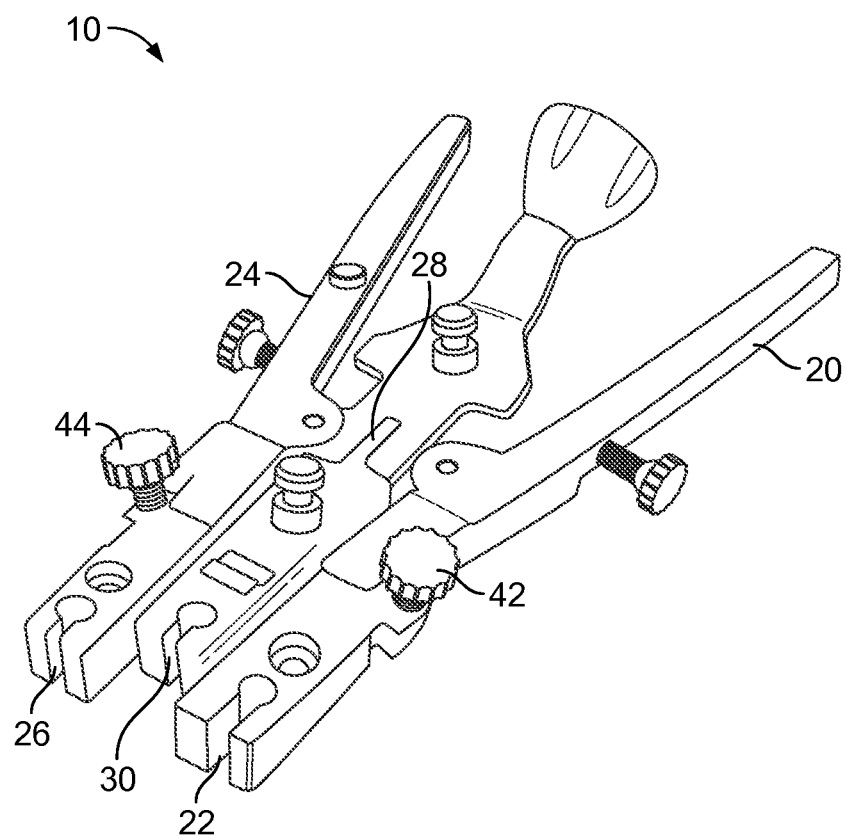
FIG. 1 is a perspective view of the retractor without blades attached in a fully closed configuration.

FIG. 1 illustrates a retractor 10 for use in a surgical procedure. The retractor 10, when in use, has a plurality of blades affixed to ends of the retractor arms of the retractor to form a retractor system 100 as shown in FIGS. 2A-3B to retract tissue in a surgical procedure to expose a surgical site such as spine during a spinal implant or repair surgery.

The refractor 10 is comprised to hold a first blade 12, a second blade 14, and a third blade 16. The first, second, and third blades 12, 14, 16 are each coupled to a refractor 10. The refractor 10 has a first rotatable arm 20 having a first blade attachment opening 22 for holding and positioning the first blade 12. The retractor 10 further has a second rotatable arm 24 having a second blade attachment opening 26 for holding and positioning the second blade 14. The retractor 10 further has a linearly translatable third arm 28 having a third blade attachment opening 30 for holding and positioning the third blade 16. The first and second rotatable arms 20, 24 and the linearly translatable third arm 28 may be actuated so that the blades 12, 14, 16 may be separated a desired distance from each other. In addition, the blade attachment openings 22, 26, and 30 may be rotated to angulate the blades 12, 14, 16, increasing the distance between the distal ends of the blades 12, 14, 16. In this manner, tissue surrounding an incision may be retracted providing access to the surgical site. In embodiments, the first, second, and third blades 12, 14, 16 may be individually articulated at the ends of each arm.

Figure 2:
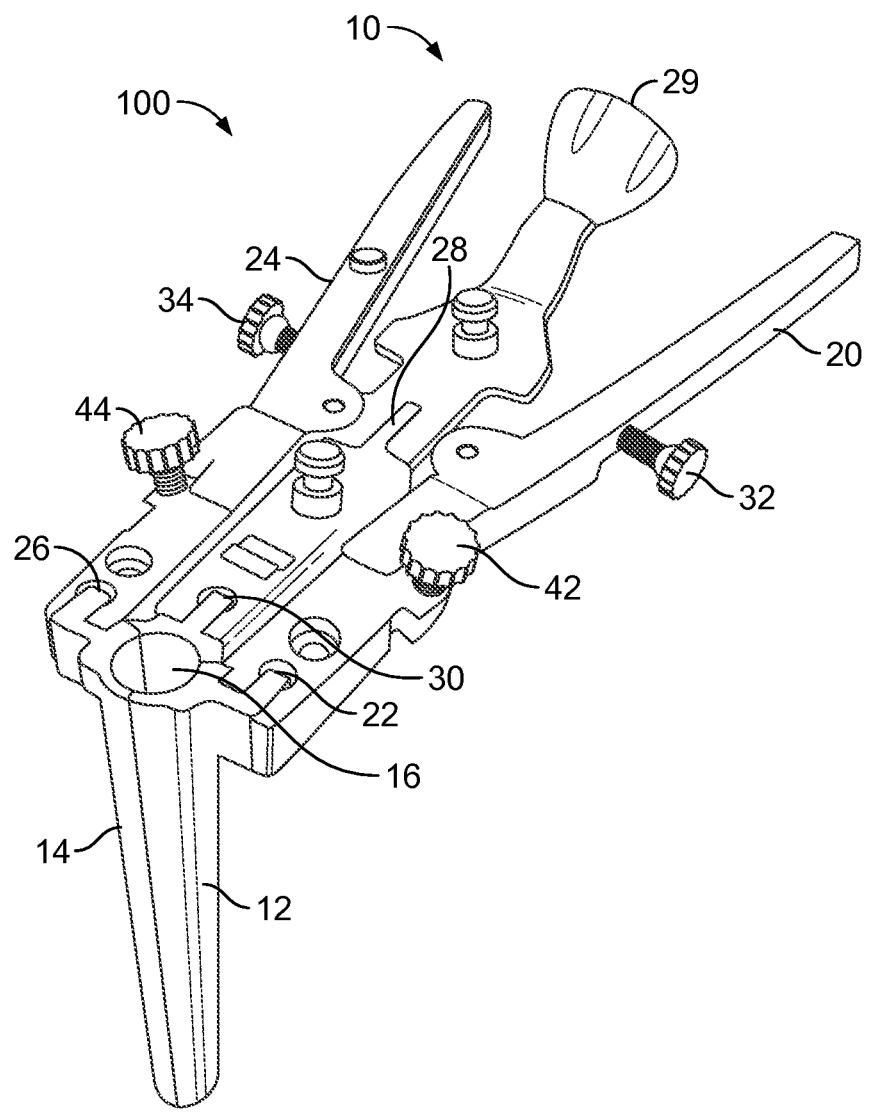
FIG. 2 is a perspective view of the retractor with three blades attached in the closed configuration showing the blades forming a generally circular shape.

FIGS. 1-2 illustrate the retractor 10 in a "closed" or non-retracted configuration, in accordance with one embodiment of the present invention. In the closed configuration, the first, second, and third blades 12, 14, 16 are radially disposed to form a small substantially closed, tube-shaped structure with a central opening 40.

Figure 2A:
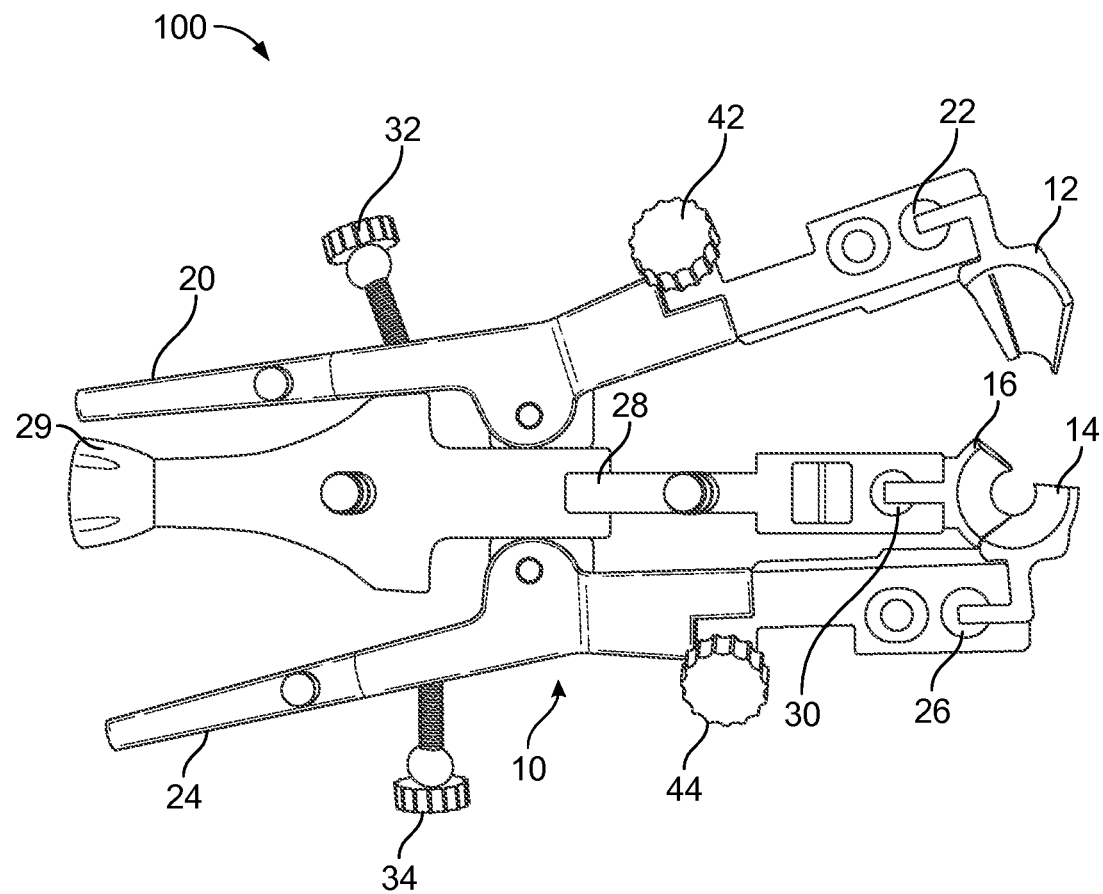
FIG. 2A is a perspective view showing a first arm in an opened configuration independent of a second arm in a closed configuration, the third arm linearly in a closed configuration.
Figure 2B:
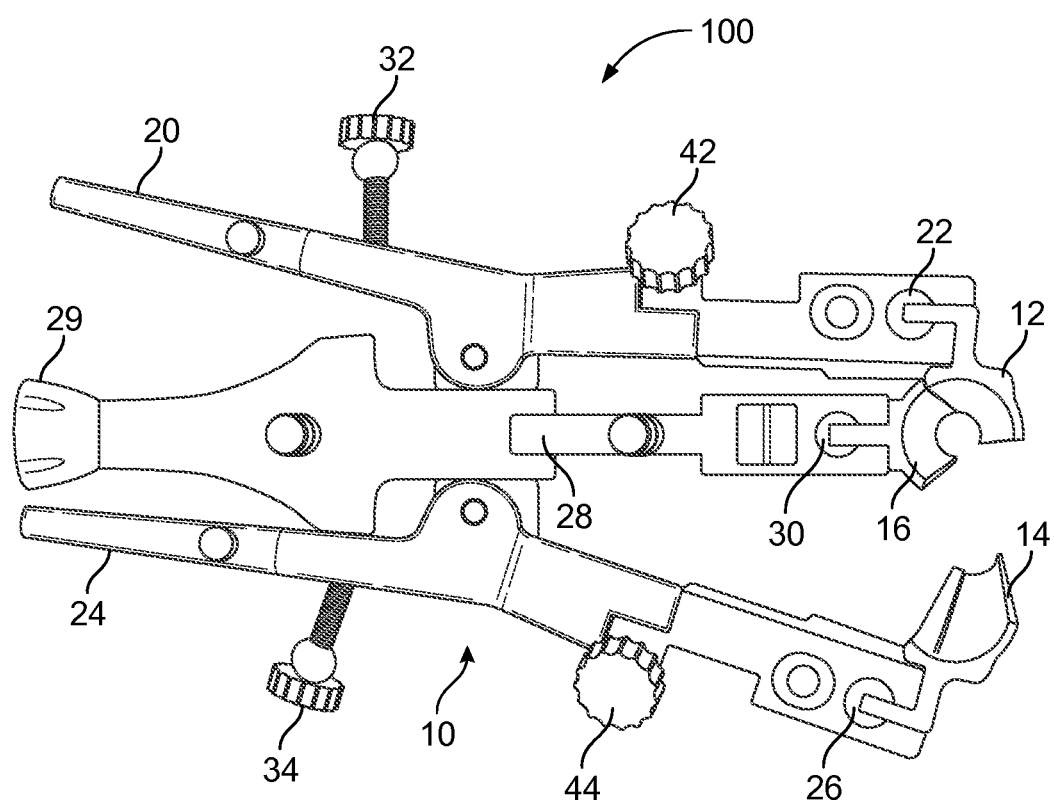
FIG. 2B is a perspective view similar to FIG. 2A only with the second arm shown in a fully open retracted configuration with the first arm shown in a closed configuration.

FIGS. 2A and 2B show a novel and most beneficial feature of the present invention refractor 10, the ability to independently move the first arm 20 relative to the stationary second arm 24 and third arm 28 and vice versa.

FIG. 2A shows the first arm 20 moved directionally to a retracted open configuration while the second arm 24 remains in a closed position. FIG. 2B shows the second arm 24 moved to an open retracted configuration while the first arm 20 is in a closed configuration.

These independent movements are facilitated by the surgeon grasping the handle outer ends of either a first or second arm and the third linearly movable arm and squeezing one of the rotatable handle ends toward the third arm handle. Thus, the surgeon can move the rotatable first blade 12 independent of the second blade 14 and vice versa.

Interestingly, when the surgeon grasps both the first and second arms 20, 24 at the handle ends 20A, 24A, he can move both arms simultaneously; however, unlike retractors that are mechanically geared together, with the present invention retractor the surgeon can squeeze both handles 20A, 24A of the first and second arms 20, 24 and feel when the tissue resistance at one blade 12 or 14 is higher than the other. Accordingly, as he squeezes further, he can independently move the tissue with less resistance to increase the surgical opening.

This ability avoids tearing or damaging the tissue and balances the forces by the greater dexterity of the skilled surgeon's hand when compared to a mechanical gear, as is used in most prior art retractor systems.

Figure 3A:
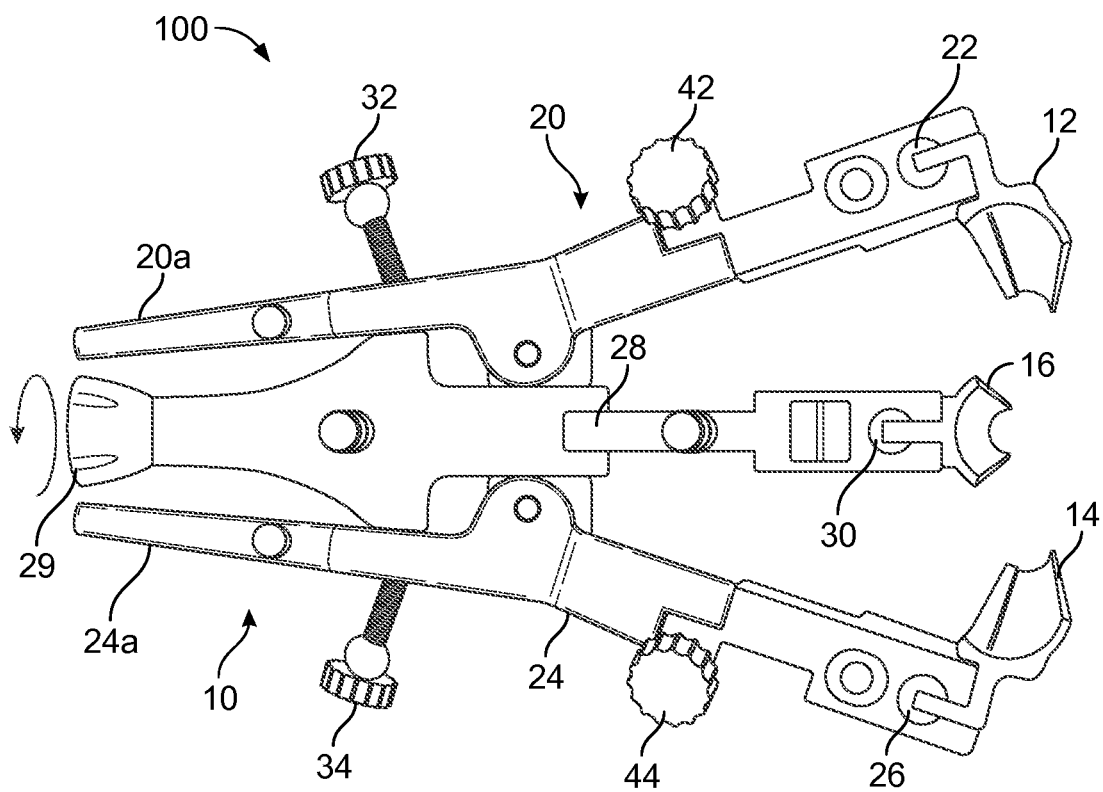
FIG. 3A is showing the first and second arm moved to a desired open configuration with the third arm linearly unmoved in a closed configuration.

In FIG. 3A, once the rotatable first arm 20 and second arm 24 are moved to the desired retracted position, each has a spring loaded adjustment screw 32, 34 that can be tightened to lock the opening between the rotatable arms 20, 24. At this time, the handle 29 on the linearly movable third arm 28, which is shown in FIG. 3A, has not been turned and the third arm 28 is still in the closed configuration. By rotating the handle 29, the third arm 28 will move linearly outwardly as shown in FIG. 3B.

Figure 3B:
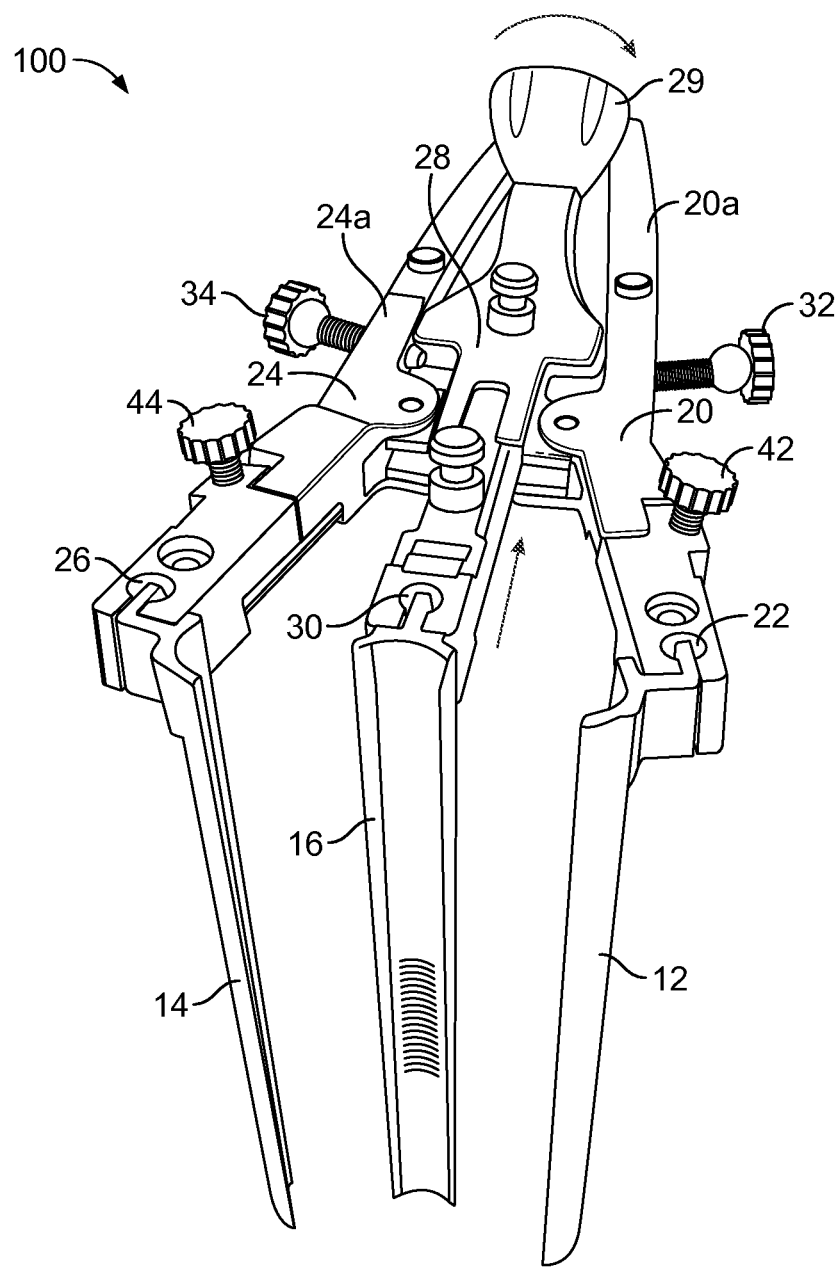
FIG. 3B is the refractor system in an open configuration showing the first and second blades in a retracted configuration as well as a linear direction arrow showing the linearly movable third arm and third blade movable towards a further retracted direction when the handle is rotated directionally as indicated.

FIG. 3B illustrates the retractor 10 in an "open" or retracted configuration. In the open configuration, the first, second, and third blades 12, 14, 16 are moved so that they no longer form a tube-shaped structure that is substantially closed. Rather, the first and second blades 12, 14 have been rotated and, if desired, angulated by adjusting knobs 42, 44 and third blade 16 has been linearly translated and angulated to enlarge the diameter of the central bore about which the blades 12, 14, 16 are arranged to expose the surgical site. In FIG. 3B, the first and second blades 12, 14 are shown fully open while the linear arrow shows the refracted direction the third blade 16 will move to when the handle 29 is rotated as indicated by the directional arrow adjacent the handle.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A retractor device comprising:
   a first arm rotatable arcuately about a first pivot;
   a second arm rotatable arcuately about a second pivot;
   a third arm interposed between the first and second arm having a linearly movable blade holding end translatable inwardly and outwardly between said first and second arms, the third arm being connected to the first arm at the first pivot and the second arm at the second pivot; and
   wherein said first arm and said second arm are rotatably movable about their respective pivot independent of the other arm, wherein each of the first and second arms each has a blade holding end and an opposite handle end wherein movement of each respective handle inwardly pivots the blade holding end arcuately about the respective pivot outwardly, each first or second arm movement being independently movable about their respective pivot relative to the other arm without any mechanically geared connections to the handles and wherein independent movement of said first arm relative to said second arm or said second arm relative to said first arm is provided by holding said third arm handle end and moving said first or second arm toward said third arm handle end while said opposite arm being unmoved, and wherein simultaneously grasping and squeezing both the first and second arms at the respective handle ends together toward the third arm moves a first and second blades toward a retracted open blade position.

2. The retractor device of claim 1 wherein the third arm has a handle end opposite the blade holding end, the linearly movable blade holding end moves a third blade, the handle end being connected to move the linearly movable blade holding end.

3. The retractor device of claim 2 wherein each first and second arm has an adjustment screw that can be tightened to set or limit inward movement between the first and second arms at a respective blade holding end.

4. The retractor device of claim 3 wherein once the first arm and second arm are moved to a desired retracted position, each of the adjustment screws is tightened to set the opening between the respective first arm and second arm and by rotating a handle at the third arm end moves the third arm linearly outward causing the first and second and third blade ends to move about said respective first and second pivots toward a more open position.

5. The retractor device of claim 4 wherein tightening the adjustment screw moves said blade end of the first or second arm about said first or second pivot outwardly so at the first or second arm, the first and second and third blades no longer form a tube-shaped structure that is substantially closed.

\* \* \* \* \*